United States Patent
Burchardt

(10) Patent No.: US 7,498,299 B2
(45) Date of Patent: Mar. 3, 2009

(54) PROCOLLAGEN (III) PROPEPTIDES AND RELATED SUBSTANCES FOR TREATING FIBROTIC DISEASES

(76) Inventor: Elmar Reinhold Burchardt, Damaschkeweg 69, Wuppertal (DE) 42113

( * ) Notice: Subject to any disclaimer, the term of this patent is extended or adjusted under 35 U.S.C. 154(b) by 0 days.

(21) Appl. No.: 11/161,274

(22) Filed: Jul. 28, 2005

(65) Prior Publication Data

US 2005/0282737 A1    Dec. 22, 2005

Related U.S. Application Data

(60) Division of application No. 10/249,686, filed on Apr. 30, 2003, now abandoned, which is a continuation of application No. PCT/EP01/12663, filed on Oct. 31, 2001.

(30) Foreign Application Priority Data

Oct. 31, 2000    (DE)    ................. 100 53 870

(51) Int. Cl.
*A61K 38/00*    (2006.01)
*A61K 38/39*    (2006.01)
*C07K 14/00*    (2006.01)

(52) U.S. Cl. ............................ 514/2; 514/12; 530/356; 530/350; 424/9.1; 435/69.7

(58) Field of Classification Search .................. 514/2, 514/12; 530/356, 350; 424/9.1; 435/69.1, 435/69.7
See application file for complete search history.

(56) References Cited

FOREIGN PATENT DOCUMENTS

| EP | 0913692 | * | 5/1999 |
| WO | WO 97/08311 | * | 3/1997 |
| WO | WO9961477 | * | 12/1999 |

OTHER PUBLICATIONS

Burchardt et al., Matrix Biology vol. 17, 673-677 (1998).*
Kauschke et al., Anal. Biochem. 275, 131-140 (1999).*

* cited by examiner

*Primary Examiner*—Chih-Min Kam
(74) *Attorney, Agent, or Firm*—Gudrun E. Huckett

(57) ABSTRACT

In a method of treating a fibrotic disease, a composition is administered to a mammal an effective amount, wherein the composition contains a polypeptide selected from the group consisting of rat, mouse, and human N-terminal procollagen (III) propeptide and rat, mouse, and human C-terminal procollagen (III) propeptide and further contains a pharmaceutically tolerable carrier or dilutant.

2 Claims, 5 Drawing Sheets

Fig. 1 (I) — SEQ ID NO. 1

N-DEPMDFKINTDEIMTSLKSV<u>NGQIESLISP</u>↓<u>DGSRKNPARN</u>CRDLKFCHPELKSGEYWVDPN
QGCKLDAIKVFCNMETGETCISANPLNVPRKHWWTDSSAEKKHVWFGESMDGGFQFSYGN
PELPEDVLDVQLAFLRLLSSRASQNITYHCKNSIAYMDQASGNVKKALKLMGSNEGEFKAE
GNSKFTYTVLEDGCTKHTGEWSKTVFEYRTRKAVRLPIVDIAPYDIGGPDQEFGVDVGPVCF
L-C

Fig. 1 (II) — SEQ ID NO. 2

N-QEAVEGGCSHLGQSYADRDVWKPEPCQICVCDSGSVLCDDIICDDQELDCPNPEIPFGEC
CAVCPQPPTAPTRPPNGQGPQGPKGDPGPPGIPGRNGDPGIPGQPGSPGSPGPPGICES<u>CPTG</u>
<u>PQNYSP</u>↓<u>QYDSYDVKSG</u>-C

PROCOLLAGEN (III) PROPEPTIDES AND RELATED SUBSTANCES FOR TREATING FIBROTIC DISEASES

This aplication is a divisional of U.S. patent application Ser. No. 10/249,686 having a filing date of Apr. 30, 2003, the disclsoure of which is incorporated in its entirety into the instant application; which application Ser. No. 10/249,686 is a continuation of international application No. PCT/EP01/12663 having a filing date of Oct. 31, 2001; the disclosure of which is incorporated in its entirety into the instant application.

BACKGROUND OF THE INVENTION

This invention relates to the use of procollagen (III) propeptides and related substances for treating fibrotic diseases and a method for producing and renaturing recombinant N- and/or C-terminal procollagen (III) propeptides. Said procollagen (III) propeptides and related substances are suitable for treating fibrosis of any type, of any organ manifestation. The invention also relates to a method for producing renatured N-terminal procollagen (III) propeptide and/or C-terminal procollagen (III) propeptide.

Collagen Biosynthesis.

The collagens of types I and III are synthesized as prepropeptides and are extensively modified posttranslationally. Among the intracellular modifications are glycosylations, enzymatic hydroxylation reactions involving lysine and proline in its 3- and 4-positions. The modified propeptides spontaneously assemble into $[a_1(III)]_3$ homotrimers in the case of collagen (III). In the case of collagen type I mostly $[a_1(I)]_2 a_2(I)$ heterotrimers as well as—to a lesser extent—$[a_1(I)]_3$ homotrimers are formed. After exocytosis, the propeptides are first cleaved at the C-terminus of the nascent collagen and then at the N-terminus by a set of specific endoproteases. The cleavage resulting in the C-terminal procollagen propeptide (PIIICP) is catalyzed by the procollagen C-proteinase that hich is identical to the Bone Morphogenetic Protein-1. Different tissue-specific expression patterns of different splice variants of the BMP-1 protein have been discovered.

The N-terminal procollagen propeptide of collagen I (PINP) is cleaved off by the same N-proteinase that also digests the N-terminal procollagen propeptide of collagen type II. By contrast, N-terminal procollagen (III) propeptide (PIIINP) is cleaved by off by a proteinase activity distinct from the N-proteinase (I and II). The responsible enzyme is called procollagen N-proteinase type III.

PIIICP.

PIIICP occurs as a trimer consisting of three identical monomeric PIIICP subunits that are linked by intermolecular disulfide bridges. Theoretical structural considerations and site-directed mutagenesis experiments with so-called collagen mini genes have led to the conclusion that at least 4 and probably 6 cysteine residues of each monomeric PIIICP subunit are involved in intramolecular disulfide bridge formation. It is likely that only the cysteine residues in positions 51 and 68 are involved in intermolecular disulfide bridge formation. It has been observed, however, that the region around these cysteine residues is critical for the correct formation of intramolecular disulfide bridges because a Cys→Ser mutation in that region leads to impaired intramolecular disulfide bridge formation. On the other hand it has been observed that the trimerization of collagen (III) fibrils proceeds even when interchain cystine bridge formation has become impossible by a Cys→Ser mutation in position 51.

So far, there have been no reports about the quantification of PIIICP except in the patents: An immunoassay for procollagen-III-C-terminal propeptide (WO09924835A2 and EP00988964A1).

There are no reports about pharmacokinetic data for PIIICP. For PICP, clearance and mode of elimination have been investigated. For $^{125}$I-labeled PICP, an elimination from the serum by the mannose-6-phosphate receptor has been reported. PIIICP could also be cleared from the circulation by this receptor as PIIICP may also be glycosylated at position Asn173. This mechanism can safely be excluded for recombinant PIIICP from E. coli, however, as the protein is not glycosylated when expressed in this host.

With regard to the physiological role of PIIICP, there is no information available in the literature. With regard to the biological effects of the C-terminal propeptide of collagen type I, different effects have been described in the literature.

The nucleotide sequence of human PIIICP has been deposited in the Genebank (Accession No. X14420 and X01742). The amino acid sequence of this peptide is shown in FIG. 1(I) as an example. The propeptide sequence is indicated in the appendix in the context of the whole procollagen sequence C-terminal of the procollagen C proteinase cleavage site.

In fibroblast cell culture, a reduction of collagen production by 80% was measured when intact PICP was present at a concentration of 40 nM, while it was decreased by 30% at 10 nM. However, these changes in the protein biosynthesis very well correlated with the measured changes at the level of transcription. This lead to the speculation that PICP exerts a regulatory effect at the level of transcription.

For intact rat PICP, isolated from fibroblasts, an inhibiton of collagen biosynthesis was also demonstrated with cell cultures of hepatic stellate cells. At a concentration of 33.3 nM an inhibitory effect of 66% was measured that increased to 83% at a concentration of 133.2 nM, respectively, Changes in mRNA concentrations affected by PICP were not investigated. It was shown in this series of experiments, however, that the inhibitory effect was strongly dependent on the structure of the protein. A covalent modification of PICP induced by the exposure to acetaldehyde lead to a marked reduction of the effect on collagen biosynthesis.

The effects of overlapping synthetic polypeptides derived from the PICP sequence in a fibroblast cell culture model are reported ambiguously in the literature.

An inhibitory effect at the level of the rate of biosynthesis was observed with a polypeptide consisting of 22 amino acid residues (residues 225 to 246).

By contrast, a further polypeptide consisting of 45 amino acid residues (residues 197 to 242) lead to an increased rate of biosynthesis for collagens of types I and III as well as for fibronectin—contrary to all previous results. At a concentration of 45 µM an increase of collagen biosynthesis by a factor of 3.3 and of fibronectin biosynthesis by a factor of 6.1 was observed in human lung fibroblasts after 4 h. After 8 a maximal stimulation of collagen biosynthesis by a factor of 6- to 8-fold was measured.

However, the stimulatory effect was dependent on the degree of confluence of the cells. While an effect was observed in subconfluent fibroblast cells, this effect could not be demonstrated in confluent cells. The effects were neither cell type- nor species-specific. In further experiments the polypeptide sequence sufficient for eliciting the stimulatory effect could be reduced to a pentapeptide (amino acid residues 212 to 216). In these experiments, 80% of the maximal stimulation was observed. The effect was notably more pronounced with fibronectin (5- to 11-fold increase) in comparison with collagen type I (4- to 7-fold increase). In parallel to the experiments focused on the protein level, the mRNA concentrations of the concerned genes were investigated. For collagen as well as for fibronectin, no concentration changes were measured at the mRNA level. According to these data, the synthetic polypeptides exerted their effects on the stimulation of collagen biosynthesis at the posttranscriptional level.

In vivo experiments with PIIICP or related substances have not been reported in the literature so far.

PIIINP

PIIINP occurs as a trimer consisting of three identical monomeric PIIINP subunits that are linked by intermolecular disulfide bridges. The PIIINP molecule is structurally divided into three domains. The most N-terminally located domain (Col1) consists of a globular structure and contains several intramolecular cystine bridges. The C-terminally adjacent Col3 domain possesses a collagen-like structure characterized by periodic Gly and Pro residues. This domain assembles into a characteristic triple-helical collagen-like structure. The Col2 domain encompasses those parts of the procollagen telopeptide region that are N-terminal of the N-proteinase cleavage site. The monomeric PIIINP strands are assembled parallel to each other in this region.

Characteristically, the Col2 domain contains two cysteine residues that are both involved in intermolecular disulfide bridge formation and that are of eminent importance for the trimeric structure of PIIINP. An oligosaccharide glycosylation site is located in the vicinity of the N-proteinase (III) cleavage site. Eight amino acid residues C-terminal of the propeptide cleavage site, one of the four lysyl residues is located which are oxidatively desaminated into aldehydes before the collagen fibrils become covalently crosslinked.

A special characteristic of collagen type III is that a fraction of the N-terminal propeptides is not cleaved off the procollagen trimer. This so-called pN-collagen type III is still incorporated into fibrils. The form of these fibrils is described in the literature in different ways: as thin fibrils that are associated with collagen type I or as pearl necklace-like fibrils that associate to become net-like structures. Electron-microscopically, pN-collagen of type III has the appearance of a "barbed wire". The presence of pN-collagen type III on the surface of collagen fibrils could play a role in the regulation of the diameter of the fibrils.

With regard to the stability of PIIINP in the body, half lives between 2 min and 239 min have been reported. The determined values varied considerably depending on the model and/or the labelling of the antigen. In rats a clearance of the N-terminal propeptide of collagens III and I from the serum—independently of the antigen species—by the scavenger receptor on liver endothelial cells has been reported (Melkko 1994). Endocytosis was mediated by the same receptor for both proteins.

The amino acid sequence of human PIIINP is deposited in the Genebank database with the accession number X14420. As an example, the amino acid sequences of this propeptide are shown in FIG. 1(II). The propeptide sequence is indicated in the context of the whole procollagen sequence N-terminal of the procollagen N proteinase type III cleavage site.

PIIINP has so far mostly been described as a marker of fibrosis. It can be used in the context of possible therapies of liver fibrosis as a possible non-invasive parameter to follow the course of the disease.

For PIIINP, research about its role as a feedback inhibitor of collagen biosynthesis in cell culture systems and in cell-free lysates has been published. For the N-terminal propeptides of collagens type I and type III as well as for the Col 1 domain of PINP, a concentration-dependent cell-specific inhibition of collagen production of the $a_1(I)$ and $a_2(I)$ chains has been measured in the fibroblast cell culture system. Protein concentrations from 0.5 µM to 6 µM were used. The inhibition was in the range between 30% to 50% in comparison with control experiments. In these experiments experimental evidence was provided that the rate of translation was influenced by the propeptides and by their fragments. These data were supported by the localization of the internalized proteins in the vicinity of the endoplasmatic reticulum.

In addition, experiments with the Col 1 domains of both N-terminal propeptides were carried out in the cell-free reticulocyte system. Protein concentrations ranging from 0.4 to 3.2 µM were used. A concentration-dependent inhibition of collagen (I) synthesis was measured. In both cases, an inhibition between 38% and 71% in comparison with control experiments was measured. When very high protein concentrations (8 µM) were used, it was demonstrated that the inhibitory effect on collagen translation could not be further increased.

When the mechanism of action of PINP was investigated a system for the recombinant cyotosolic expression of PINP in fibroblast cell culture was also examined. While the measured collagen (I) mRNA concentration was unchanged, the rate of biosynthesis of the corresponding protein was reduced. It was therefore regulated at the post transcriptional level.

These results for PINP are supported by experiments with skin fibroblasts from dermatosparactic sheep. In the homologous human disease, Ehlers Danlos syndrome of type VIIa or VIIb, a mutation within the N-proteinase cleavage site of procollagen type I occurs. Consequently, PINP cannot be cleaved off. In cell culture, these cells which lack the PINP feedback mechanism in comparison with heterozygous control fibroblasts, displayed a proportion of 15 to 20% of collagen biosynthesis compared to the total cellular biosynthesis (control fibroblasts 2 to 4%).

Recombinant Production of Procollagen III Propeptides.

The recombinant production of procollagen (III) propeptides has been reported in a number of publications. The recombinant production of a collagen $a_2(I)$ mutant in so-called A2 cells derived from the rat liver epithelial cell line W8 which is in turn deficient for collagen $a_2(I)$ is described. The recombinant expression of collagen $a_1(III)$ minigenes has been described more recently.

Recently, the production of PIIICP in Zf9 cells as a trimeric protein has been described. The recombinant protein could only be produced in small quantities for analytical purposes, however. The recombinant production of PIIICP in *E. coli* was described in the patent applications: An immunoassay for procollagen-III-C-terminal propeptide (WO09924835A2 and EP00988964A1) and in Burchardt, 1998. The yields were above 20 mg/l fluid culture medium with this expression method. The majority of the recombinant protein was in the form of inclusion body protein, however, and had to be purified using denaturing methods of dissolution. The expressed proteins also contained an N-terminal His tag, so that they could be purified in denaturing solvents over a Ni-NTA column. For chronic in vivo applications, these proteins were less suitable because of the potential immunogenicity of the His tag and because the biological half-life of the recombinant proteins may be decreased for this reason. They occurred mostly in a monomeric form when the methods disclosed in this application were used. Their solubility was too low for most therapeutic applications. When a concentration of approximately 10 µg/ml was exceeded, the recombinant PIIICP precipitated from aqueous solutions.

The recombinant expression of human PIIINP in *E. coli* has been described in the patent application: Monoclonal antibody and assay for detecting PIIINP (WO09961477A2), and the expression of murine PIIINP has been reported in Kauschke, 1999. The yields were at approximately 5 mg/l fluid culture medium with this expression method. These expressed proteins also contained an N-terminal His tag , so that they could be purified in denaturing solvents over a Ni-NTA column. For chronic in vivo applications, these proteins were also less suitable because of the potential immunogenicity of the His tag and because the biological half-life of the recombinant proteins may be decreased for this reason. The solubility of PIIINP in aqueous solutions was too low for most therapeutic applications.

Fibrotic Diseases.

Fibrotic diseases are defined as a diverse group of diseases that are associated with a qualitatively altered collagen production or with an increased deposition of collagen in the exrtracellular space. To this group of diseases belong, among others, systemic or localized scleroderma, liver fibrosis of various etiologies, alcoholic cirrhosis, e.g. alcoholic liver cirrhosis, biliary cirrhosis, hepatitis of viral or other origin, veno-occlusive disease, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, keloids, hypertrophic scars, joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, atherosclerotic alterations, pulmonary hypertension, angiopathy of the arteries and veins, aneurysms of large vessels.

Further fibrotic diseases are induced or initiated by scar revisions, plastic surgeries, glaucoma, cataract fibrosis, corneal scaring, graft vs. host disease, tendon surgery, nerve entrapment, Dupuytren's contracture, OB/GYN adhesions, pelvic adhesions, infertility, peridural fibrosis, diseases of the thyroid gland or the parathyroids, metastatic bone disease, multiple myeloma, or restenoses. In many of the aforementioned diseases, a successful therapy has not been established so far. In others, a need for improved approaches or for the reduction of undesired side effects exists.

From the aforementioned it follows that there is a further need to supply efficacious drugs against fibrotic diseases. The solution to this task is achieved by the embodiments presented in the examples.

SUMMARY OF THE INVENTION

Thus the present invention relates to a composition; preferably a medicament, containing (a) a (poly) peptide which is the N-terminal procollagen (III) propeptide and/or the C-terminal procollagen (III) propeptide or (b) a fragment or derivative thereof with mainly the antifibrotic activity of the (poly) peptide (a) and/or (c) a peptide which contains the recognition sequence of procollagen C-proteinase of type III and/or a peptide that contains the cleavage sequence of procollagen N-proteinase of type III, in combination with a pharmaceutically tolerable carrier or diluent.

The term "(poly)peptide which is the N-terminal procollagen (III) propeptide and/or the C-terminal procollagen (III) propeptide" means in the light of the invention that the (poly) peptide is the N-terminal or C-terminal procollagen (III) propeptide to which further amino acid sequences can be added N-terminally or C-terminally so that a longer (poly) peptide is generated. The additional sequences can be derived from procollagen or can be heterologous or artificial sequences. Preferred are (poly) peptides that contain possible procollagen C- or N-proteinase-recognized cleavage sites in addition to the (human) PIIICP or PIIINP amino acid sequence.

The term "a fragment or derivative thereof with mainly the antifibrotic activity of the (poly) peptide (a)" means in the light of the invention that this fragment or derivative thereof has at least 50%, preferably 75%, more preferred 85%, and especially preferred 90% of the antifibrotic activity of the N-terminal or C-terminal procollagen propeptide. Derivatives of the (poly) peptide may contain other amino acids than the natural amino acids or substituted amino acids. For example, derivatives can be obtained from peptidomimetics.

While the following embodiments are commonly discussed in the context of medicaments, they also apply mutatis mutandis to the compositions.

The term "(poly) peptide" applies to polypeptides as well as to peptides. A peptide commonly contains not more than 30 amino acids.

Possible procollagen C-proteinase recognition sequences are indicated in FIG. 1(I).

Possible procollagen-N-proteinase recognition sequences are indicated in the PIIINP sequence in FIG. 1(II).

Examples of suitable pharmaceutically tolerable carriers and/or diluents are known to the specialist and encompass for example phosphate-buffered saline solutions, water, emulsions, as for example oil/water emulsions, different kinds of detergents, sterile solutions, etc. Medicaments that contain such carriers can be formulated by known conventional methods. These medicaments can be administered to the individual at a suitable dose. The administration route can be oral or parenteral, for example intravenous, intraperitoneal, subcutaneous, intramuscular, local, intranasal, intrabronchial, oral or intradermal, or via a catheter at a location inside of an artery. Formulations for a parenteral administration encompass sterile aqueous or non-aqueous solutions, suspensions and emulsions. Examples of non-aqueous dilutants suitable for injections are propylene glycol, polyethylene glycol, plant oils, as for example olive oil, and organic esters, as for example ethyloleate. Aqueous carriers encompass water, alcoholic aqueous solutions, emulsions, suspensions, salt solutions and buffered media. Parenteral carriers encompass sodium chloride solutions, Ringer Dextrose, Dextrose and sodium chloride, Ringer Lactate, and bound oils. Intravenous carriers encompass, for example, fluid-, nutrient- and electrolyte-additives (as for example those that are based on Ringer Dextrose). The medicament can also contain preservatives and other additives, as for example antimicrobial compounds, antioxidants, complex forming substances and inert gases. Furthermore, it may contain other active agents, for example interleukins, growth factors, differentiation factors, interferons, chemotactic proteins, or an unspecific immunomodulatory agent.

The kind of dosing is determined by the treating physician according to clinical factors. It is known to the specialist that the kind of dosing is dependent on different factors, e.g. body height or weight, respectively, the body surface, age, sex, or the general state of health of the patient, but also on the agent to be administered specifically, the duration and kind of administration, and on other medicaments that are possibly administered in parallel. A typical dose can for example be in the range between 0.001 and 1000 µg, whereby doses above and below this exemplary range are imaginable, in particular taking into account the factors mentioned above. Commonly, the dose should be in the range between 1 µg and 10 mg per day when the formulation of the invention is administered regularly. Commonly, the agents will be present at a concentration of more than 10 μg/ml in a physiological buffer in these formulations. They can, however also be present in a solid state at a concentration of 0.1 to 99.5% (weight/weight) in the final mixture. Commonly, it has proved to be of advantage to apply the agent(s) in total amounts of approximately 0.001 mg/kg to 100 mg/kg, preferably in total amounts of 0.01 mg/kg to 10 mg/kg body weight per 24 hours, as a continuous infusion or as several single administrations, to achieve the desired results. When the formulation is applied intravenously the dose should be in the range between 1 μg and 10 mg units per kilogram body weight per day. The medicament can be applied locally or systemically.

Surprisingly, it was discovered in the present invention that the above mentioned (poly) peptides, and PIIICP in particular, are taken above in the liver in vivo and display antifibrotic activity. The mechanism of action of recombinant PIIICP by downregulation of connective tissue growth factor mRNA was surprising as well and unexpected. The role of PIIICP as a natural feedback inhibitor of fibrotic matrix deposition was described for the first time here. The findings of the invention were furthermore surprising because PIIICP/PIIINP were so far, for the most part, only discussed as diagnosis markers to monitor the effectiveness of other medicaments, but not in the context as a therapeutic agent for use in humans. The achieved antifibrotic effect was thus entirely surprising.

In vivo experiments to ameliorate fibrotic diseases by administration of recombinant PIIINP have not been described in the literature so far. Because of the lacking glycosylation of recombinant PIIINP from *E. coli* the reduction of the fibrotic area described in this application was utterly surprising and unexpected.

In a preferred embodiment the (poly) peptide or fragment or derivative and/or peptide stems from human procollagen (III) or is derived from it.

In a further preferred embodiment the recognition sequence-containing (poly) peptide contains 10 to 15 amino acids N-terminal of the cleavage site.

In an additional preferred embodiment the recognition sequence-containing (poly) peptide contains 10 to 15 amino acids C-terminal of the cleavage site.

In a further preferred embodiment the (poly)peptide is a fusion protein.

In an especially preferred embodiment the (poly)peptide contains a His tag. The His tag can be added C-terminally or N-terminally.

In a further especially preferred embodiment the His tag is a 6 His tag and is added N-terminally.

Furthermore, the present inventions relates to the use of the afore described (poly) peptide or fragment or derivative thereof to manufacture a medicament or medical device to treat or prevent fibrotic diseases.

In a preferred embodiment the fibrotic diseases are chosen from systemic or localized scleroderma, liver fibrosis of various etiologies, alcoholic cirrhosis, e.g. alcoholic liver cirrhosis, biliary cirrhosis, hepatitis of viral or other origin, veno-occlusive disease, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, keloids, hypertrophic scars, joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, atherosclerotic alterations, pulmonary hypertension, angiopathy of the arteries and veins, aneurysms of large vessels or are induced or initiated by scar revisions, plastic surgeries, glaucoma, cataract fibrosis, corneal scaring, graft vs. host disease, tendon surgery, nerve entrapment, Dupuytren's contracture, OB/GYN adhesions, pelvic adhesions, infertility, peridural fibrosis, diseases of the thyroid gland or the parathyroids, metastatic bone disease, multiple myeloma, or restenoses.

Furthermore, the present invention relates to a method to produce renatured N-terminal procollagen (III) propeptide and/or C-terminal procollagen (III) propeptide, where (a) inclusion bodies are produced in *E. coli* employing to commonly known methods, where the inclusion bodies are dissolved in a 0.5 to 8 M denaturing buffer; (b) the buffer according to (a) is pipetted dropwise into a limited dilution buffer that is buffered around neutral pH and contains L-Arginine in a final concentration between 200 to 1,000 nM and a disulifide bridges-reducing coupled redox system, until a volume ratio of the denaturing buffer to the limited dilution buffer of maximally 1:3 is reached, respectively; (c) the buffer mixture according to (b) is dialyzed against a physiological buffer that contains L-Arginine at a final concentration of 50 to 200 nM and a disulfide bridges-reducing coupled redox system for at least 2 hours; (d) the buffer mixture according to (c) is dialyzed against a physiological buffer that contains a disulfide bridges-reducing coupled redox system for at least 2 hours; and (e) the buffer mixture according to (d) is dialyzed against a physiological buffer for at least 2 hours.

It follows that the buffer of step (d) contains no Arginine and in step (e) neither Arginine nor the redox system.

The possibility to dissolve recombinant PIIICP in higher concentrations than previously described in physiological buffer was completely surprising and unexpected because it is known to the specialist that collagens are hard to dissolve in physiological buffers.

By this method the therapeutic application of recombinant procollagen propeptides and of related substances in therapeutically relevant concentrations becomes possible. In example 4 the use of procollagen propeptides that were renatured according to this method in animal models of liver fibrosis is described.

In a preferred embodiment a chelator is added to the buffer in at least one of the steps (b) to (d). Preferably the chelator is EDTA, for example at a final concentration of 10 mM.

In a further preferred embodiment the redox system consists of reduced Glutathione-oxidized Glutathione. It is especially preferred that the components of the redox system of example 2 occur at the concentrations disclosed in example 2.

In another preferred embodiment a protease inhibitor is added to the buffer in at least one of the steps (b) to (d). Preferred is the protease inhibitor Pefabloc SC.

In an additional preferred embodiment a salt is added to the buffer in one of the steps (b) and/or (d) at a final concentration of approximately 10 mM. Preferably, the salt is NaCl. It is especially preferred that the limited dilution buffer and the dialysis buffer are of the concentrations disclosed in example 2.

In an further preferred embodiment the denaturing buffer of step (a) contains urea at a final concentration from 0.5 to 8 M. Preferentially, the buffer contains urea at a final concentration of approximately 6 M.

In another preferred embodiment Trizma-Base is used as a buffer.

In an additional preferred embodiment the dialysis steps are carried out at approximately 4° C.

In another preferred embodiment the dialysis is carried out against at least 100 times the volume of the dialysate in steps (c) to (e).

In addition, the present invention relates to a method to produce a medicament wherein the renatured N-terminal procollagen (III) propeptide and/or C-terminal procollagen (III) propeptide, which is produced according to claims 10 to 18, is concentrated according to common methods or lyophilised, and a pharmaceutically tolerable carrier or pharmaceutically tolerable diluent is added.

Suitable, pharmaceutically tolerable carriers and dilutants have been discussed previously.

Furthermore, the present invention relates to the use of an N-terminal procollagen (III) propeptide and/or C-terminal procollagen (III) propeptide which is produced according to the methods disclosed in the invention, to treat or prevent fibrotic diseases.

In a preferred embodiment fibrotic diseases are chosen among systemic or localized scleroderma, liver fibrosis of various etiologies, alcoholic cirrhosis, e.g. alcoholic liver cirrhosis, biliary cirrhosis, hepatitis of viral or other origin, veno-occlusive disease, idiopathic interstitial fibrosis, idiopathic pulmonary fibrosis, interstitial pulmonary fibrosis, acute pulmonary fibrosis, acute respiratory distress syndrome, perimuscular fibrosis, pericentral fibrosis, dermatofibroma, kidney fibrosis, diabetic nephropathy, glomerulonephritis, keloids, hypertrophic scars, joint adhesions, arthrosis, myelofibrosis, corneal scaring, cystic fibrosis, muscular fibrosis, Duchenne's muscular dystrophy, esophageal stricture, retroabdominal scaring, Crohn's disease, ulcerative colitis, atherosclerotic alterations, pulmonary hypertension, angiopathy of the arteries and veins, aneurysms of large vessels or are induced or initiated by scar revisions, plastic surgeries, glaucoma, cataract fibrosis, corneal scaring, graft vs. host disease, tendon surgery, nerve entrapment, Dupuytren's contracture, OB/GYN adhesions, pelvic adhesions, infertility, peridural fibrosis, diseases of the thyroid gland or the parathyroids, metastatic bone disease, multiple myeloma, or restenoses.

The tables show the following.

Table 1 shows the body weight at the end of the experiment, the relative liver weight, GIDH serum activities, collagen types III and I as well as TGF-$b_1$ mRNA concentrations after chronic application of different procollagen $a_1$(III) propeptides in the mouse $CCl_4$ model. mRNA concentrations after TaqMan analysis are presented as $\Delta$ ct values in comparison with the intact control (mean +/−SEM).

Table 2 shows the body weight at the end of the experiment, the relative liver weight, GIDH serum activities collagen types III and I as well as TGF-$b_1$ mRNA concentrations after chronic application of different concentrations of the PIIICP4.1 protein in the mouse $CCl_4$ model. MRNA concentrations after TaqMan analysis are presented as $\Delta$ ct values in comparison with the intact control (mean +/−SEM).

TABLE 1

| Group | PIIICP4.1 [500 µg/ml] | PIIINP 4.5.2 [500 µg/ml] | M1 [500 µg/ml] | Fibrosis Control | Intact Control |
|---|---|---|---|---|---|
| Final Body Weight [g] | 26.25 ± 0.75 | 24.29 ± 0.81 ($p < 0.03$) | 25.56 ± 0.38 | 26.22 ± 0.32 | 30.25 ± 0.63 |
| Liver Weight [g/100 g body weight] | 6.52 ± 0.13 | 6.44 ± 0.16 | 6.42 ± 0.12 | 6.12 ± 0.12 | 5.13 ± 0.26 |
| GIDH Activity [U/ml Serum] | 3715 ± 268 | 3983 ± 305 | 3977 ± 312 | 4480 ± 269 | 12 ± 4 |
| Collagen $a_1$(III) mRNA-Conc. | 3.32 ± 0.32 | 2.53 ± 0.37 | 3.05 ± 0.28 | 2.76 ± 0.29 | 0.00 ± 0.24 |
| Collagen $a_1$(I) mRNA-Conc. | 4.62 ± 0.35 | 4.27 ± 0.18 | 5.13 ± 0.33 | 4.36 ± 0.33 | 0.00 ± 0.12 |
| TGFb$_1$ mRNA-Concentration | 1.40 ± 0.51 | 2.71 ± 0.48 | 1.99 ± 0.44 | 2.11 ± 0.26 | 0.00 ± 0.35 |

TABLE 2

| Group | PIIICP4.1 [50 µg/ml] | PIIICP4.1 [150 µg/ml] | PIIICP4.1 [500 µg/ml] | Fibrosis Control | Intact Control |
|---|---|---|---|---|---|
| Final Body Weight [g] | 25.88 ± 0.30 | 25.33 ± 0.88 | 26.00 ± 0.856 | 24.50 ± 1.17 | 29.63 ± 0.38 |
| Liver Weight [g/100 g body weight] | 6.94 ± 0.26 | 7.01 ± 0.27 | 7.66 ± 0.29 | 6.83 ± 0.31 | 5.62 ± 0.22 |
| GIDH Activity [U/ml Serum] | 589 ± 77 | 522 ± 33 ($p < 0.05$) | 578 ± 115 | 867 ± 126 | 32 ± 14 |
| Collagen $a_1$(III) mRNA-Conc. | 2.27 ± 0.17 | 2.20 ± 0.42 | 1.98 ± 0.34 | 1.79 ± 0.52 | 0.00 ± 0.30 |
| Collagen $a_1$(I) mRNA-Conc. | 3.85 ± 0.21 | 3.58 ± 0.46 | 3.72 ± 0.41 | 3.25 ± 0.58 | 0.00 ± 0.41 |

BRIEF DESCRIPTION OF THE DRAWINGS

FIG. 1(I) depicts the amino acid sequence SEQ ID NO. 1 around the human C-terminal procollagen (III) propeptide (PIIICP). The N-terminal end of the prosequence is formed by the procollagen C-proteinase cleavage site (designated by the arrow). The propeptide sequence itself is printed in bold letters. The section of the sequence in the vicinity of the procollagen C-proteinase cleavage site is underlined. FIG. 1(II) shows the amino acid sequence SEQ ID NO. 2 around the human N-terminal procollagen (III) propeptide (PIIINP). The N-terminal end of the prosequence borders to the presequence. The procollagen N-proteinase cleavage site is designated by an arrow. The propeptide sequence itself is printed in bold letters. The part of the sequence in the vicinity of the procollagen N-proteinase cleavage site is underlined.

FIG. 5A shows intact control after 7 days of infusion of a buffer control solution (240-fold magnification); FIG. 5B shows $CCl_4$-induced liver fibrosis after 7 days of infusion of PIIICP protein (400-fold magnification); FIG. 5C shows $CCl_4$-induced liver fibrosis after 7 days of infusion of a buffer control solution (fibrosis control, 320-fold magnification).

DESCRIPTION OF PREFERRED EMBODIMENTS

Figure 2:
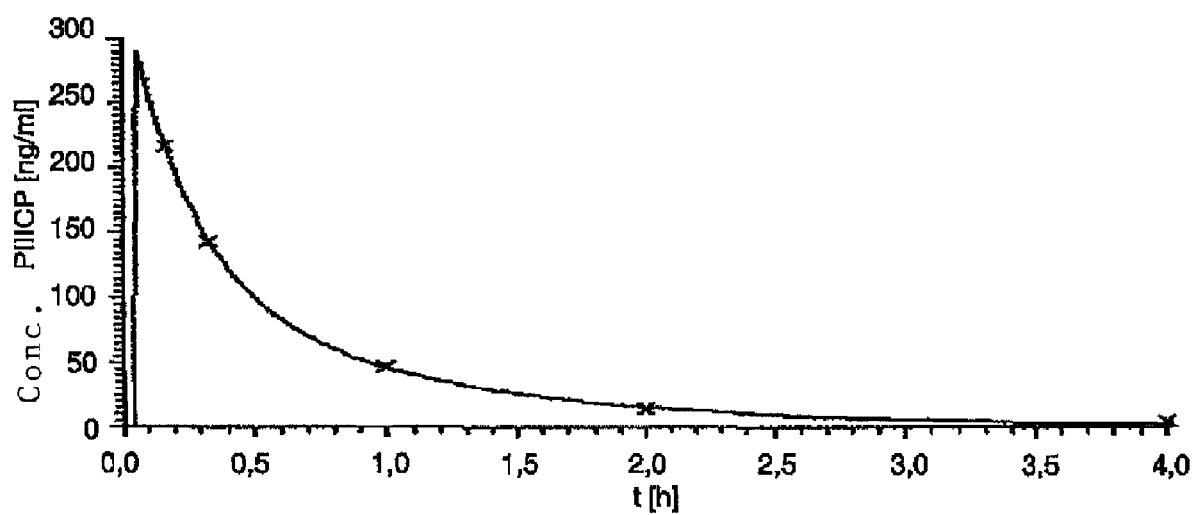
FIG. 2 shows the time course of PIIICP serum concentrations in the model of the anaesthetized rat. The terminal half life time was approximately 80 min, the terminal distribution volume was at approximately 7.4 l/kg and the elimination rate at approximately 6.3 l/(h*kg). For details refer to example 3 of the present invention.

In this description a number of documents are cited. The disclosed content of these documents, including instructions of the manufacturer, is hereby incorporated by reference.

In the examples "v/v" denotes volume percentage and "w/v" denotes weight percentage.

EXAMPLE 1

Purification of PIIICP from Inclusion Bodies in *E. coli*

PIIICP was produced in the form of inclusion bodies in *E. coli* (Burchardt 1998). The cell pellets from three 200 ml cell cultures were resuspended in 24 ml 50 mM Tris-HCl (pH 8.0) 1 M NaCl, frozen over night at −20° C. and centrifuged at 5,000 g for 10 minutes after thawing. 4.8 ml of the same buffer were added to the precipitate and 4.8 ml of a 25 mM Tris-HCl (pH 8.0), 5 mg/ml lysozyme as well as 4.8 ml of a 0.5 M EDTA solution (pH 8.0) were added. After 1 hour of incubation at 37° C. the bacteria cells were disintegrated by ultrasonification. Subsequently, 12 ml of 10% Triton-X-100, 1 mM EDTA, dissolved in 50 mM Tris HCl (pH 8.0), were added and after 30 min of incubation the mixture was centrifuged at 5,000 g for 10 minutes. The unsoluable fraction was dissolved by ultrasonification in 24 ml 5% Triton-X-100, dissolved in 50 mM Tris-HCl (pH 8.0), incubated at 37° C. one more time and was again centrifuged at 5,000 g for 10 minutes. The triton extraction was repeated once to remove the membrane lipids. Subsequently, the pellet was dissolved by ultrasonification in 24 ml 1 M urea, 1 mM EDTA, dissolved in 50 mM Tris HCl (pH 8.0) and centrifuged again after 30 minutes of incubation (5,000 g, 10 min). The pellet almost entirely consisted of almost pure PIIICP in the form of inclusion bodies. The protein could be dissolved in 6 M urea, in turn dissolved in 50 mM Tris-HCl (pH 8.0). When the sample was centrifuged for 30 minutes at 15,800 g, the inclusion body protein remained in the supernatant.

EXAMPLE 2

Renaturation of Recombinant Collagen a1(III) Propeptides

As an example, recombinant human PIIICP4.1 was renatured, the production of which was described in Burchardt, 1998, and in the patents: An immunoassay for procollagen-III-C-terminal propeptide (WO09924835A2 and EP00988964A1). Furthermore, recombinant human PIIINP 4.5.2 was renatured, the production of which was described in the patent: Monoclonal antibody and assay for detecting PIIINP (WO09961477A2). Finally, recombinant murine PIIINP, the production of which was described in Kauschke, 1999, was renatured using the method described below.

However, the method is not limited to the renaturation of these exemplary propeptides, but is suitable for the renaturation of other procollagen propeptides and similar compounds.

Method.

Used Buffers.

A) Dialysis buffer.

300 mM Trizma-Base, pH 7.4

400 mM L-Arginine 10 mM EDTA 0.4 mM Pefabloc SC 1 mM Glutathione reduced 0.1 mM Glutathione oxidized.

B) Limited Dilution Buffer.

50 mM Trizma-Base, pH 7.4

800 mM L-Arginine 10 mM NaCl 10 mM EDTA 0.4 mM Pefabloc SC 1 mM Glutathione reduced 0.1 mM Glutathione oxidized.

Collagen $a_1$(III) propeptides can be dissolved in 6 M urea buffer. In a limited dilution step the buffer conditions were abruptly altered for the proteins. A redox system present in the buffer facilitated the formation of disulfide bridges. To this effect, the protein solution was added dropwise to a surplus of ice-cold limited dilution-buffer while being gently shaken. This solution was stored over night at 4° C.

All dialysis steps were performed at 4° C. At every step the dialysis was performed for at least three hours and against a one-hundredfold buffer volume. The limited dilution solution was transferred into a tube of suitable pore size and dialyzed against the dialysis buffer. In the following dialysis steps the L-Arginine concentration was lowered to 100 mM, subsequently a buffer without L-Arginine was used. In addition, the fourth buffer was lacking the Glutathione redox system. The final buffer was chosen according to the intended use. For in vivo experiments, for example, it consisted of 10 mM Trizma-Base, pH 7.4, 145 mM NaCl. The dialysate was finally stored at 4° C.

EXAMPLE 3

Measurement of the Elimination Kinetics of Renatured PIIICP in the Anaesthetized Rat Materials and Methods.

PIIICP-Plate-ELISA: The determination of PIIICP concentrations in biological samples was carried out with a sandwich ELISA assay. Two monoclonal anti-PIIICP antibodies were used (Burchardt, 1998).

As a catching antibody, antibody 48B14 (Burchardt, 1998) was immobilized on an ELISA plate at a concentration of 5 µg/ml. After blocking free unspecific binding sites on the plate by incubation with a 3% (v/v) BSA solution, biological samples or buffered solutions with known PIIICP concentrations were added together with a known concentration of a FITC-labelled secondary antibody (48D19) (Burchardt, 1998) for 30 minutes to the immobilized secondary antibody. Remaining free PIIICP antigen and free secondary antibody were subsequently removed by washing steps and the amount of bound, labelled secondary antibody was determined. The aforementioned antibodies can be replaced by other anti-PIIICP antibody couples that can be produced according to commonly used practices.

The measured in vivo concentrations in human serum were for the most part below the limit of detection (below 0.5 ng/ml, see the patent application: An immunoassay for procollagen-III-C-terminal propeptide (WO09924835A2 and EP00988964A1)). These results are almost an order of magnitude below the phsysiological PIIINP concentrations in human serum.

Animal experiment: Fastened Sprague-Dawley rats with a body weight of approximately 300 g were anaesthetized by intraperitoneal administration of Trapanal at 100 mg/kg body weight.

Fluids or dilutions of the substances were applied through a catheter placed into the jugular vein. The measurement of the blood pressure as well as the drawing of blood were performed via a femoral artery catheter. To facilitate spontaneous breathing the tracheae of the animals were canalized. During the experiments the animals received infrared heat radiation. After initiation of the surgical procedures, the animals received 5 ml of physiological salt solution per kg body weight as a bolus to compensate for the loss of blood. After a recovery period of 15 minutes, the substance dilutions in physiological buffer (10 mM Trizma-Base, pH 7.4, 145 mM NaCl) were administered for 2 hours by continuous infusion of renatured PIIICP4.1 (Burchardt, 1998) at a flow rate of 100 µl per kg body weight and minute (The PIIICP4.1 concentration in the infusion solution was approximately 150 µg/ml). Blood samples were drawn after 2 min, 60 min, 115 min, 150 min, 180 min and 225 min after the start of the infusion. This was paralleled by a recording of the blood pressure. At each time point 400 µl of blood were drawn and immediately 20 µl of heparin (250 IE/ml) were added, the sample was centrifuged at high speed and the plasma was stored at −20° C. until testing. After the experiment the experimental animals were sacrificed by application of a KCl solution. The pharmacokinetic parameters were determined subsequent to the PIIICP concentration measurements in the samples.

Results.

The terminal half life time was determined as approximately 80 minutes. In the terminal area of the curve approximately 6.1% of the total area were under the curve. The distribution volume in the terminal phase was at approximately 7.4 l/kg and the rate of elimination was determined at approximately 6.3 l/h/kg (see FIG. 2).

EXAMPLE 4

Demonstration of the Biological Efficacy of PIIICP and PIIINP

The biological efficacy of the compounds can be demonstrated in cell culture assays and in vivo. For example, after addition of the inhibitors to human cell lines, a drop in the concentration of free α1(III) propeptide in the supernatant can be measured because the peptide is released by the enzymatic activity of PCP. To measure PIIICP concentrations in the supernatant a recently established assay can be used (Burchardt, 1997, and patent application: An immunoassay for procollagen-III-C-terminal propeptide (WO09924835A2 and EP00988964A1)).

In this patent the biological efficacy of PIIICP4.1 (production described in Burchardt, 1998, and in the patents: An immunoassay for procollagen-III-C-terminal propeptide (WO09924835A2 and EP00988964A1), purification and renaturation described above in this patent as an example); of PIIINP4.5.2 (production described in the patent: Monoclonal antibody and assay for detecting PIIINP (WO09961477A2), renaturation described above in this patent as an example) and of murine recombinant PIIINP (production described by Kauschke, 1999, renaturation described above in this patent as an example) are described as examples in the model of the $CCl_4$-induced liver fibrosis of the mouse.

For PIIICP the antifibrotic effect of 3 different doses of this compound in this animal model is described as an example.

Depending on the organ manifestation or the kind of fibrotic damage animal models with other fibrosis manifestations, for example in the heart, in the kidney, in the lungs, in the skin, or in other organs can be used.

In the example of the $CCl_4$-induced liver fibrosis of the mouse the reduction of the collagen deposition brought about by PIIICP and PIIINP is described by quantitative morphometry. It can also be carried out by determination of the hydroxyprolin content of the fibrotic organs or by quantitative morphometry (Kauschke, 1999). In addition, the organ-protective effective effect of PIIICP and PIIINP by reduction of cell damage is described in the example, as determined by measurement of the activities of intracellular marker enzymes (e.g. GIDH). The measurement of the organ-protective effect can also be carried out in a different way, for example by measurement of inhibition of the extent of apoptosis or necrosis or such.

Materials and Methods.

Animal experiments: The experimental animals received 0.2 ml per 100 g body weight of a mixture of $CCl_4$ and mineral oil in a ratio of 1:8 twice per week. The substance was administered by daily intraperitoneal application of 0.5 ml of a dilution of the substance. The fibrosis- and the intact-controls received a buffer control solution without procollagen propeptides. The animals had free access to standard diet and water during the whole experiment. The body weight of the animals was measured at the beginning and at the end of the experiment. Upon termination of the experiment the wet weight of the liver was determined, the liver was portioned for the subsequent experiments and immediately shock-frozen in liquid nitrogen. It was stored until use at −80° C. In addition, plasma samples were drawn from the experimental animals to determine clinical chemistry parameters with them.

Total collagen staining with Sirius Red/Fast Green: 14 µm frozen sections were dried over night. After a 10 minute treatment with a 10% (v/v) formaldehyde solution the slices were washed twice for 5 minutes with $H_2O$ dest., respectively. The Picrosirius Red staining was carried out for 30 minutes at room temperature in a 0.1% (w/v) Sirius Red solution in saturated picric acid (per 400 ml a PBS tablet and 10 ml of concentrated acidic acid were added). The sections were again washed with $H_2O$ dest. twice and subsequently stained in a 0.1% (w/v) Fast Green solution in saturated picric acid (per 400 ml a PBS tablet and 10 ml of concentrated acidic acid were added). The unstaining and dehydratization steps consisted of a sequence of washing steps: 10 seconds $H_2O$ dest., 10 seconds 70% (v/v) ethanol, a minute 80% (v/v) and 90% (v/v) ethanol, respectively, three times with pure ethanol for two minutes, respectively. Before they were covered with the Leica CV Mount, the sections were washed three times in xylol for 5 minutes.

Total RNA preparation from tissue: Approximately 20 mg of tissue were pulverized in liquid nitrogen and transferred into an Eppendorf tube. 600 µl of RLT buffer (with 0.1% (v/v) b-mercaptoethanol) were added to the powdered tissue, mixed to homogeneity, and the mixture was applied on a QIAshredder column. The column was centrifuged at 18,000 g and 4° C. for 2 minutes. The retained solid constituents were discarded, and the flow through was further used. The subsequent processing steps were carried out with the RNeasy Total RNA Kit (Qiagen, Hilden) according to the manufacturer's recommendations. The elution steps was carried out with 35 µl of RNase-free $H_2O$. The RNA content of each preparation was determined directly thereafter in an aliquot, a further aliquot was examined for the integrity of the obtained RNA bands using an RNA formaldehyde agarose gel. The samples were stored at −80° C. until use.

cDNA synthesis from total RNA: The synthesis of cDNA from the prepared total RNA samples was performed with the SuperScript preamplification system according to the manufacturer's (Gibco BRL) recommendations in all cases. All working steps were carried out on ice. In all cases, 1 µg of total RNA and master mixes were used. Before the reverse transcription potentially present impurities consisting of genomic DNA were removed from all samples by digestion with DNase I. For this purpose 1 µg of total RNA solution was brought up to a volume of 8 µl with RNase-free water, 1 µl of DNase I solution (Superscript kit) and 1 µl of 10× buffer were added and the digest was incubated for 10 minutes at room temperature. The DNase I digest was stopped by the addition of 1 µl of 25 mM EDTA solution and subsequent incubation (10 minutes at 65° C.). The whole volume was used in the cDNA synthesis. Subsequent to the cDNA synthesis the volume was brought up to 100 µl total volume with DNase-free water and stored at −80° C. until use. In all cDNA synthesis procedures, controls without the addition of reverse transcriptase were carried out randomly to check for contaminations consisting of genomic DNA.

Determination of mRNA concentrations by a TaqMan PCR analysis: The determination of specific mRNA concentrations was carried out by a TaqMan analysis. During the PCR reaction a specific hybridizing fluorescent probe is cleaved—by the exonuclease activity of the Taq polymerase—and the resulting fluorescent signal is measured in real time. The results are presented as the number of cycles when the measured specific fluorescent signal exceeds the threshold value for the first time. Smaller ct values indicate that a higher specific mRNA concentration had been present in the original sample. Maximally achievable is a doubling of the amount of product during each cycle. By choosing suitable primers and probes, and a small length of the amplified sequence, approximately a doubling of the amount of product can be assumed in each PCR cycle during the exponential phase of the reaction. Consequently, using the measured differences in the ct values, differences in the mRNA concentrations of the respective transcript in the original sample can be calculated after calibration. Thus, a calibrated difference of 3 ct units means that the mRNA concentrations of this transcript are differing from the reference samples by a factor of $8 (=2^3)$ when the assumption of a doubling of the amount of product during each PCR cycle is valid.

With regard to the mRNA concentrations, all measured mRNA concentrations were calibrated based on the respective HPRT mRNA concentration. For the HPRT mRNA concentration it was possible to show that it remains unaltered during the course of a fibrotic disease and that HPRT can be used as a standard, meaning as a reference level.

All primers and probes were so chosen, with respect to their localization on the gene and to the expected amplification product that a doubling of the concentration of the product in each cycle was to be expected in the course of a TaqMan PCR reaction. These assumptions were checked by control experiments before and verified. The primers and the 6-FAM-labeled probes were all present at concentrations of 100 µM. To prevent variability between the different incubations master mixes were used in all cases and every incubation was carried out at least in duplicate. Determinations of every single transcript were carried out for all samples on the same plate. In all experiments, control experiments without template or without previous reverse transcription were carried out. All work was performed on ice. The master mix contained 12.5 µl of the TaqMan Universal Master Mix (Roche), 7.5 µl of the primer-probe-mix (1 µM with respect to each primer and 0.5 µM probe in DNase/RNase-free water) as well as 3.75 µl DNase/RNase-free water. Per determination, 2.5 µl cDNA solution were pipetted into 96 well plates with optical lids and mixed with 22.5 µl of the master mix. The plates were centrifuged for 1 minute at 500 g and 4° C. The program of the TaqMan PR reaction encompassed a heating phase of 2 minutes at 50° C., a 10 minute denaturing step at 95° C. as well as 40 cycles with a denaturing step at 95° C. for 15 seconds and a combined one minute annealing/expansion step at 60° C. Within the cycles, the fluorescence of the liberated fluorescent probe was measured automatically at the time point of the denaturation step. The evaluation was carried out with the ABI PRISM Sequence Detection Software. The baseline was set at the mean of cycles 3 and 15, the threshold was 0.04.

Results.

Effects of the infusion of procollagen (III) propeptides in the chronic i.p. experiment in the mouse $CCl_4$ model: To investigate the effect of the recombinantly produced procollagen a1(III) propeptides on the formation of an experimentally induced liver fibrosis groups of 10 mice were treated with $CCl_4$ only or with protein solutions at concentrations of 500 µg/ml, respectively. In addition, one group received buffer control solution only (intact control). As therapeutic recombinant proteins, human PIIICP4.1 (production described in Burchardt, 1998, and in the patent applications: An immunoassay for procollagen-III-C-terminal propeptide (WO09924835A2 and EP00988964A1)), purification and renaturation described above in this patent application as an example); complete human PIIINP4.5.2 (production described in the patent: Monoclonal antibody and assay for detecting PIIINP (WO09961477A2); renaturation described above in this patent as an example); and murine PIIINP containing 18 amino acid residues of the prosequence (designated M1, production described by Kauschke, 1999, renaturation described above in this patent application as an example) were used.

At the end of the treatment the dissolved PIIICP in the infusion solution was not degraded in all cases. This was demonstrated with an SDS PAGE gel.

In all animals, the relative collagen area with respect to the total area was determined morphometrically in liver sections as well as the GIDH activity in the serum and the mRNA concentration of selected transcripts by a TaqMan analysis.

The proteins were well tolerated by the animals over the studied time period in the concentrations used. There were no pathologic signs, furthermore an increased mortality did not occur.

Figures 3A, 3B:
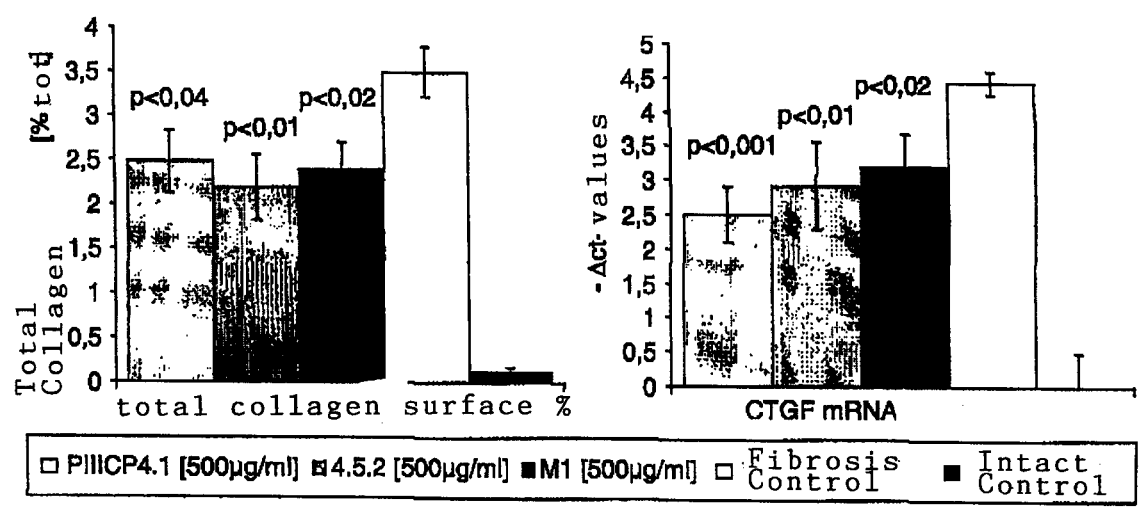
FIG. 3A shows the fraction of the collagen area with respect to the total area and FIG. 3B the CTGF mRNA concentration after chronic application of various procollagen $_1$(III) propeptides in the mouse $CCl_4$ model (mean±SEM).

The morphometrically determined relative collagen area with respect to the total area, as determined by automated analysis of the Sirius Red-stained area, showed the highest values in the fibrosis control group (Kauschke, 1999). In the treatment groups the relative collagen area with respect to the total area was significantly reduced in all cases (FIG. 3A). With PIIICP4.1, to 71% of the fibrosis control (p<0.04); with PIIINP4.5.2 to 63% of the fibrosis control (p<0.01); and with M1 to 68% of the fibrosis control (p<0.02).

When the CTGF mRNA concentrations in the liver are regarded, a significant reduction in concentration in the treatment groups in comparison to the fibrosis control was observed (FIG. 3B). The differences were approximately +1.9 Δ ct-units (PIIICP4.1, p<0.001), approximately +1.5 Δ ct-units (PIIINP4.5.2, p<0.01), and approximately +1.2 Δ ct-units (M1, p<0.02).

The GIDH serum activity was also reduced in all treatment groups in comparison to the fibrosis control (Table 1) (Kauschke 1999). The serum activities were 17% (PIIICP 4.1) or 11% (PIIINP4.5.2, M1), respectively, lower than in the fibrosis control. Due to individual variations the differences did not reach the level of significance (p<0.05) in any case.

In all cases with $CCl_4$ application a reduction in body weight (Table 1) was observed. Differences between the treatment groups and the fibrosis control were not observed.

The relative liver weight was above the intact controls in all $CCl_4$ groups. Treated animals tended to present with slightly higher relative liver weights in comparison to the fibrosis control. The absolute liver weights were not significantly different among the groups (Table 1).

The mRNA concentrations of the transcripts for collagens type III and type I, $TGFb_1$ (Table 1) as well as for lysyl oxidase, MMP-1, PAI-1, and tenascin (data not shown) revealed no significant differences between the fibrosis control group and the treatment groups receiving the procollagen $a_1$(III) propeptide applications.

More detailed studies on the in vivo effects of the recombinantly produced PIIICP 4.1 protein: To investigate the effect of the recombinantly produced procollagen $a_1$(III) propeptides (production described in Burchardt, 1998, and in the patent applications: An immunoassay for procollagen-III-C-terminal propeptide (WO09924835A2 and EP00988964A1), purification and renaturation described above in this patent application as an example) on the formation of an experimentally induced liver fibrosis were carried out in the mouse $CCl_4$ model.

Groups of 8 mice were treated with $CCl_4$ only (fibrosis control), or additionally with PIIICP4.1 protein solutions with concentrations of 50 μg/ml PIIICP4.1, of 150 μg/ml and of 500 μg/ml over a period of 14 days, respectively. In addition, on group was treated with buffer solution only (intact control).

At the end of the treatment the dissolved PIIICP in the infusion solution was not degraded in all cases. This was demonstrated with an SDS PAGE gel.

In all animals, the relative collagen area with respect to the total area was determined morphometrically in liver sections, as well as the GIDH activity in the serum and the mRNA concentrations of selected transcripts by TaqMan analysis.

The proteins were well tolerated by the animals over the studied time period in the concentrations used. There were no pathologic signs, furthermore an increased mortality did not occur.

In all animals with $CCl_4$ application a reduction in body weight was observed in comparison with the untreated control animals at the end of the experiment (Table 2). However, when comparing between the fibrosis control and the PIIICP groups significant differences were not observed. There was merely a tendency towards higher body weights in the animals receiving PIIICP applications, independently of the received concentration.

The relative liver weight was higher in all $CCl_4$-treated groups than in the untreated intact control. There were no significant differences when the single treatment groups were compared to the fibrosis control (Table 2).

Figures 4A, 4B:
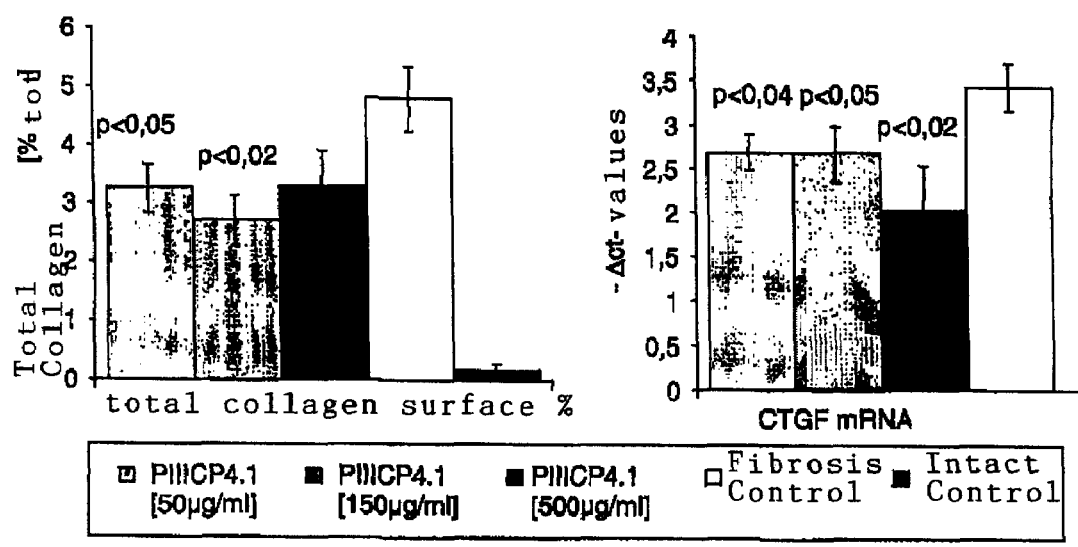
FIG. 4A shows the fraction of the collagen area with respect to the total area and FIG. 4B the CTGF mRNA concentration after chronic application of different concentrations of the PIIICP4.1 protein in the mouse $CCl_4$ model (mean±SEM). For details refer to example 4 of the present invention.

When the total collagen deposition as determined by automatic analysis of the Sirius Red-stained areas is regarded, significant differences between the different groups of animals were revealed (FIG. 4A). After chronic treatment with i.p.-injected renatured PIIICP4.1 solution a reduction in the total collagen area was measured in all treatment groups. In the treatment groups with the lowest PIIICP dose (50 μg/ml) the total collagen area was reduced significantly by 32% in comparison with the fibrosis control (p<0.05). After a treatment with 150 μg/ml PIIICP 4.1 the significant reduction was 44% with respect to the fibrosis control (p<0.02). The treatment group with the highest protein concentration (500 μg/ml PIIICP 4.1) exhibited marked variations of the measured total collagen area within the treatment group and showed a reduction of the total collagen area by 31%. The level of significance (p<0.05) was not reached in comparison with the fibrosis control.

The clinical parameter GIDH activity was determined in the serum in parallel as a measure of the degree of cell damage and was markedly reduced in the groups that received additional PIIICP4.1 protein solution in comparison with the fibrosis control (Table 2). After chronic treatment with 50 μg/ml PIIICP4.1 GIDH serum activity was 68% of the activity in the fibrosis control, after 150 μg/ml PIIICP it was at approximately 60% of the fibrosis control and after 500 μg/ml it was at approximately 67% of the fibrosis control. Only at 150 μg/ml was the reduction significant in comparison with the fibrosis control (p<0.05). In the other two treatment groups the level of significance was not reached due to variations of the results from one animal to the other, respectively.

After calibration based on HPRT, differences between the intact control animals (without $CCl_4$ application) and the fibrosis control were observed with all transcripts (collagen type I, collagen type III, tenascin, PAI-1, MMP-1, lysyl oxidase, and CTGF). All examined transcripts were genes that participate in the synthesis of the extracellular matrix. Consequently, the mRNA concentrations were on the average by the factor of 6 to 10 higher in the fibrosis controls than in the intact controls.

Significant differences between those animals that were treated with PIIICP4.1 in addition to the $CCl_4$ damage and the fibrosis control were measured for the CTGF transcript among all examined transcripts (FIG. 4B). At 50 μg/mlPII-ICP4.1 the difference was at approximately +0.74 Δ ct-units ($p<0.04$), at 150 µg/ml at approximately +0.75 Δ ct-units ($p<0.05$) and at 500 µg/ml PIIICP4.1 at approximately +1.41 Δ ct-units ($p<0.02$).

EXAMPLE 5

Immunohistochemical Detection of PIIICP on Liver Sections
Materials and Methods.

Liver fibrosis model of the bile duct-ligated rat: In fastened female Sprague-Dawley rats the main bile duct was isolated after medial opening the upper abdomen medially during barbiturate anaesthesia. By means of an inserted catheter the bile duct system was occluded by the application of approximately 0.1 ml Ethibloc per animal. The bile duct was subsequently ligated distally and proximally and dissected. Intact control animals were also operated, the bile duct system was not occluded, however.

The PIIICP4.1 application (production described in Burchardt, 1998, and in the patent applications: An immunoassay for procollagen-III-C-terminal propeptide (WO09924835A2 and EP00988964A1), purification and renaturation described above in this patent application as an example) was performed by a permanent venous infusion via an implanted permanent catheter.

The implantation of a femoral vein catheter was performed in parallel to the bile duct occlusion. For this purpose the skin was opened in the right inguinal region and the femoral vein was atraumatically isolated and fixated by two ligatures. After incision a venous catheter was inserted towards the heart and fixated. The catheter was subsequently directed towards the collar subcutaneously by means of a trocar and the surgical wound was closed by a skin suture. The venous catheter was connected to a rotation adapter by a necklace through a protective spiral. It was coupled to an infusion pump. For infection prophylaxis 0.1 ml of Tardomycel were applied subcutaneously following the surgery.

The initiation of the PIIICP4.1 infusion at a concentration of 300 µg/ml took place 24 h after the surgery. The intact- and fibrosis controls received buffer control infusions. The infusion was performed at a rate of 0.2 ml per hour over a time period of seven days. The infusion solution was kept cool (approximately 7° C.) over the entire time period of the experiment.

The rats were kept in a round cage with free access to standard diet and water. The body weight of the animals was recorded at the beginning and at the end. At the end of the experiment the liver was portioned for subsequent experiments and immediately shock-frozen in liquid nitrogen and stored at −80° C. until use.

Fixation of the tissue for immunohistochemistry: For immunohistochemical studies the tissues were fixated for 24 h in a 3.6% formaldehyde solution (v/v). After washing with destined water the water was extracted with increasing concentrations of ethanol and the tissues were embedded in paraffin at 52° C.

Immunohistochemistry: 5 µm paraffin sections were deparaffinized. For this purpose the sections were immersed successively in xylol, pure ethanol, and in a concentration series of an ethanol-water mixture (90% (v/v), 80% (v/v) 70% (v/v)) and subsequently transferred into pure water. After a five minute treatment with 3.6% (v/v) $H_2O_2$ they were washed with destined $H_2O$. Subsequently they were washed for five minutes with PBS. Blocking was performed for 20 minutes in a solution of 5% (w/v) dry milk powder and in 1% (w/v) BSA in PBS. After washing twice for three minutes in PBS the primary antibody (monoclonal mouse anti-PIIICP-antibody 48D19) was added at a concentration of 4 µg/ml in PBS and incubated for an hour at room temperature. After two further washing steps the next steps were performed according to the ExtrAvidin Staining Kit (Sigma Aldrich). The sections were incubated with biotinylated anti mouse IgG's in a 1:15 dilution in PBS with 1% (w/v) for 20 minutes at room temperature. After two washing steps they were treated with a 1:15 dilution of ExtrAvidin Peroxidase for 20 minutes at room temperature. This dilution was prepared using PBS with an addition of 1% (w/v) BSA. Following two washing steps the sections were developed for 10 minutes with the DAB system (1 tablette per 5 ml of water, respectively) (Sigma Aldrich). Residual staining solution was removed with $H_2O$ dest. The counterstaining of the cell nuclei was performed using hematoxylin. The tissue sections were placed into acidic Mayer's hematoxylin (1:4 dilution in $H_2O$ dest.), the stain was subsequently washed out with $H_2O$ dest. The sections were rinsed with tab water for 5 minutes to develop the bluish color of hematoxylin. After a washing step with $H_2O$ dest. the sections were dehydrated. Using aqueous ethanol solutions of increasing concentrations the water was extracted (70% (v/v), 80% (v/v), 90% (v/v), finally three times with pure ethanol). The dehydrated sections were washed three times with xylol for 5 minutes and were embedded with the Leica CV Mount artificial resin.

Results.

FIG. 5 shows immunohistochemical studies with the anti-PIIICP antibody 48D19 on representative sections from rat livers. A liver fibrosis was induced by a bile duct ligation. Subsequently, a PIIICP protein solution or a buffer control solution was infused for a period of 7 days through a permanent catheter.

Figures 5A, 5B, 5C:
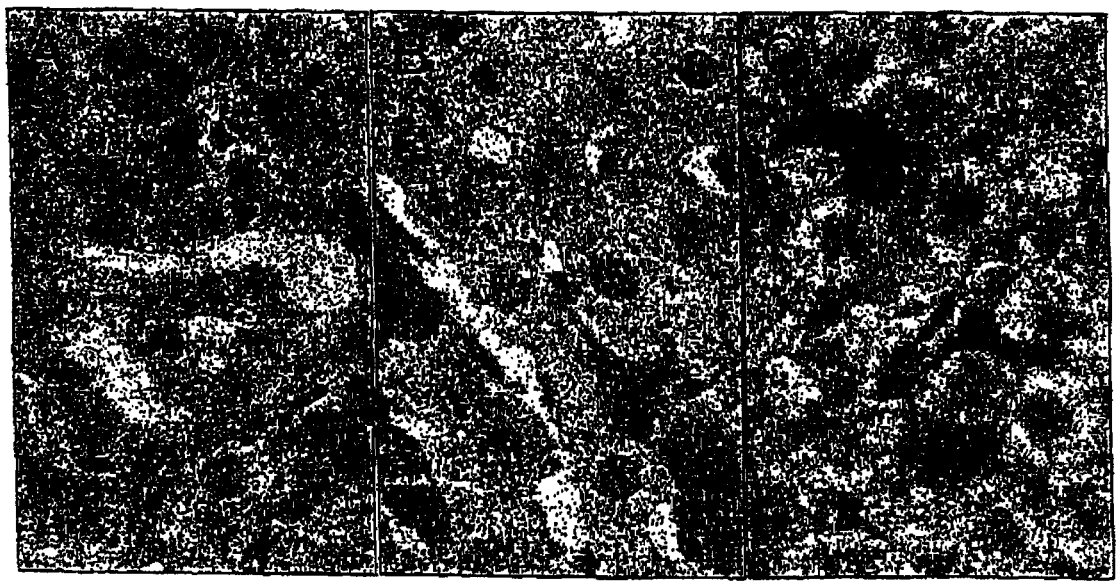
FIG. 5A to FIG. 5C show immunohistochemical studies on the localization of the PIIICP antigen on representative sections from rat livers. The monoclonal antibody 48D19 was used.

In the intact control, namely sham-operated animals infused with a buffer control solution, immunohistochemical staining with the PIIICP antibody was hardly discernable (FIG. 5A).

The fibrosis control revealed heavy damages to the liver (FIG. 5C). A massive proliferation of the bile ducts was observed in the damaged livers. In the area of the hepatic sinoids single cells, that proved positive for smooth muscle cell actin (a-SMA) on control sections, were stained heavily. They were transformed hepatic stellate cells that were stained selectively. The hepatic sinoids were markedly reduced in their perfusion capacity. A staining of hepatocytes was not observed.

On sections from animals with bile duct ligation and PIIICP infusion a strong intracellular staining of hepatic stellate cells was also observed (FIG. 5B). In contrast to the fibrosis control, these cells showed additional intracellular staining in the shape of granula. This intracellular staining was in these cases also detected in hepatocytes with access to the sinoids. As far as can be seen, there was no specific immune reaction in the cell nucleus. The extent of fibrosis was less than in the fibrosis control.

Literature.

Burchardt E R et al. Monoclonal antibody and assay for detecting PIIINP. WO09961477A2.

Burchardt E R et al. An immunoassay for procollagen-III-C-terminal propeptide. WO09924835A2 and EP00988964A1.

Burchardt E R, Schröder W, Heke M, Kohlmeyer J, Neumann R, Kroll W (1997) Expression cloning of C-terminal procollagen (III) propeptide and its use in a novel serum assay to monitor liver fibrogenesis. Hepatology 26: 487A.

Burchardt E R, Heke M, Kauschke S G, Harjes P, Kohlmeyer J, Kroll W, Schauer M, Schroeder W, Voelker M (1998)

Epitope-specific monoclonal antibodies against human C-terminal procollagen α₁(III)-propeptide. Matrix Biology 17: 673-677.

Kauschke S G, Knorr A, Heke M, Kohlmeyer J, Schauer M, Theiss G, Waehler R, Burchardt E R (1999) Two assays for measuring fibrosis: RT-PCR of collagen alpha1 type III is an early predictor of subsequent collagen deposition while a novel N-terminal procollagen (III) propeptide assay reflects manifest fibrosis in $CCl_4$-treated rats. Analytical Biochemistry 275: 131-140.

What is claimed is:

1. A method of treating fibrotic liver disease comprising the step of administering to a mammal an effective amount of a composition to reduce fibrotic matrix deposition, the composition comprised of:
   a polypeptide comprising amino acid residues 1 to 129 of the amino acid sequence SEQ ID NO:2 and optionally comprising a recognition sequence for affinity purification; and
   a pharmaceutically tolerable career or dilutant.

2. A method of reducing fibrotic matrix deposition in fibrotic diseases comprising the step of administering to a mammal an effective amount of a polypeptide comprising amino acid residues 1 to 129 of the amino acid sequence SEQ ID NO:2 and optionally comprising a recognition sequence for affinity purification.

* * * * *

```
                        SEQUENCE LISTING

<160> NUMBER OF SEQ ID NOS: 2

<210> SEQ ID NO 1
<211> LENGTH: 245
<212> TYPE: PRT
<213> ORGANISM: Homo sapiens
<220> FEATURE:
<221> NAME/KEY: CHAIN
<222> LOCATION: (1)..(30)
<223> OTHER INFORMATION: C-terminal telopeptide region N-terminally
      adjacent to C-proteinase cleavage site
<220> FEATURE:
<221> NAME/KEY: SITE
<222> LOCATION: (21)..(40)
<223> OTHER INFORMATION: possible C-proteinase cleavage recognition
      sequence
<220> FEATURE:
<221> NAME/KEY: SITE
<222> LOCATION: (30)..(31)
<223> OTHER INFORMATION: C-proteinase cleavage site
<220> FEATURE:
<221> NAME/KEY: PROPEP
<222> LOCATION: (31)..(245)
<223> OTHER INFORMATION: C-terminal procollagen (III) proptide sequence
<300> PUBLICATION INFORMATION:
<308> DATABASE ACCESSION NUMBER: EMBL
<309> DATABASE ENTRY DATE: 1989-11-23
<313> RELEVANT RESIDUES: (1)..(245)
<300> PUBLICATION INFORMATION:
<308> DATABASE ACCESSION NUMBER: EMBL / X14420
<309> DATABASE ENTRY DATE: 1989-11-23
<313> RELEVANT RESIDUES: (1)..(245)

<400> SEQUENCE: 1

Asp Glu Pro Met Asp Phe Lys Ile Asn Thr Asp Glu Ile Met Thr Ser
1               5                   10                  15

Leu Lys Ser Val Asn Gly Gln Ile Glu Ser Leu Ile Ser Pro Asp Gly
                20                  25                  30

Ser Arg Lys Asn Pro Ala Arg Asn Cys Arg Asp Leu Lys Phe Cys His
            35                  40                  45

Pro Glu Leu Lys Ser Gly Glu Tyr Trp Val Asp Pro Asn Gln Gly Cys
    50                  55                  60

Lys Leu Asp Ala Ile Lys Val Phe Cys Asn Met Glu Thr Gly Glu Thr
65                  70                  75                  80

Cys Ile Ser Ala Asn Pro Leu Asn Val Pro Arg Lys His Trp Trp Thr
                85                  90                  95

Asp Ser Ser Ala Glu Lys Lys His Val Trp Phe Gly Glu Ser Met Asp
            100                 105                 110

Gly Gly Phe Gln Phe Ser Tyr Gly Asn Pro Glu Leu Pro Glu Asp Val
        115                 120                 125

Leu Asp Val Gln Leu Ala Phe Leu Arg Leu Leu Ser Ser Arg Ala Ser
    130                 135                 140

Gln Asn Ile Thr Tyr His Cys Lys Asn Ser Ile Ala Tyr Met Asp Gln
145                 150                 155                 160

Ala Ser Gly Asn Val Lys Lys Ala Leu Lys Leu Met Gly Ser Asn Glu
                165                 170                 175
```

-continued

Gly Glu Phe Lys Ala Glu Gly Asn Ser Lys Phe Thr Tyr Thr Val Leu
            180                 185                 190

Glu Asp Gly Cys Thr Lys His Thr Gly Glu Trp Ser Lys Thr Val Phe
            195                 200                 205

Glu Tyr Arg Thr Arg Lys Ala Val Arg Leu Pro Ile Val Asp Ile Ala
            210                 215                 220

Pro Tyr Asp Ile Gly Gly Pro Asp Gln Glu Phe Gly Val Asp Val Gly
225                 230                 235                 240

Pro Val Cys Phe Leu
            245

<210> SEQ ID NO 2
<211> LENGTH: 139
<212> TYPE: PRT
<213> ORGANISM: Homo sapiens
<220> FEATURE:
<221> NAME/KEY: PROPEP
<222> LOCATION: (1)..(129)
<223> OTHER INFORMATION: N-terminal procollagen (III) propeptide
<220> FEATURE:
<221> NAME/KEY: SITE
<222> LOCATION: (120)..(139)
<223> OTHER INFORMATION: possible N-proteinase cleavage recognition site
<220> FEATURE:
<221> NAME/KEY: SITE
<222> LOCATION: (129)..(130)
<223> OTHER INFORMATION: N-proteinase proteolytic cleavage site
<220> FEATURE:
<221> NAME/KEY: CHAIN
<222> LOCATION: (130)..(139)
<223> OTHER INFORMATION: N-terminal telopeptide sequence C-terminally
      adjacent to N-proteinase cleavage site
<300> PUBLICATION INFORMATION:
<308> DATABASE ACCESSION NUMBER: EMBL
<309> DATABASE ENTRY DATE: 1989-11-23
<313> RELEVANT RESIDUES: (1)..(139)

<400> SEQUENCE: 2

Gln Glu Ala Val Glu Gly Gly Cys Ser His Leu Gly Gln Ser Tyr Ala
1               5                   10                  15

Asp Arg Asp Val Trp Lys Pro Glu Pro Cys Gln Ile Cys Val Cys Asp
            20                  25                  30

Ser Gly Ser Val Leu Cys Asp Asp Ile Ile Cys Asp Asp Gln Glu Leu
            35                  40                  45

Asp Cys Pro Asn Pro Glu Ile Pro Phe Gly Glu Cys Cys Ala Val Cys
50                  55                  60

Pro Gln Pro Pro Thr Ala Pro Thr Arg Pro Pro Asn Gly Gln Gly Pro
65                  70                  75                  80

Gln Gly Pro Lys Gly Asp Pro Gly Pro Pro Gly Ile Pro Gly Arg Asn
            85                  90                  95

Gly Asp Pro Gly Ile Pro Gly Gln Pro Gly Ser Pro Gly Ser Pro Gly
            100                 105                 110

Pro Pro Gly Ile Cys Glu Ser Cys Pro Thr Gly Pro Gln Asn Tyr Ser
            115                 120                 125

Pro Gln Tyr Asp Ser Tyr Asp Val Lys Ser Gly
            130                 135